United States Patent [19]
Paul

[11] 4,180,389
[45] Dec. 25, 1979

[54] ISOLATION AND CONCENTRATION OF SAMPLE PRIOR TO ANALYSIS THEREOF

[75] Inventor: Donald G. Paul, Landenberg, Pa.

[73] Assignee: Envirochem Inc., Kemblesville, Pa.

[21] Appl. No.: 959,638

[22] Filed: Nov. 13, 1978

[51] Int. Cl.$^2$ ............................................. B01D 15/08
[52] U.S. Cl. .......................................... 55/28; 55/67; 55/197; 55/208
[58] Field of Search ................... 210/31 C, 198 C, 28; 55/67, 197, 386, 206, 208; 73/61.1 C

[56] References Cited

U.S. PATENT DOCUMENTS

| | | | |
|---|---|---|---|
| 2,398,818 | 4/1946 | Turner | 55/67 X |
| 3,462,918 | 8/1969 | Prosser | 55/67 |
| 3,626,761 | 12/1971 | Hahuki et al. | 55/197 X |
| 3,693,403 | 9/1972 | Paul et al. | 73/30 |
| 3,847,546 | 11/1974 | Paul | 73/61.1 C |
| 3,955,924 | 5/1976 | Northmore | 23/230 PC |

*Primary Examiner*—John Adee
*Attorney, Agent, or Firm*—Peter J. Georges

[57] ABSTRACT

A method and apparatus are described for the isolation and purification of a solute prior to carrying the solute by means of a carrier gas into analytical instruments such as gas chromatographs. The apparatus is comprised of a serial differential trapping arrangement. The method provides for increasing the ratio of solute to carrier gas in a gaseous stream containing a carrier gas and a sample comprising solute. This is accomplished by forming a first gaseous stream comprising the sample, passing the first gaseous stream into a first adsorbent-containing trap and therein trapping said solute; and, thereafter simultaneously heating and backflushing said first trap with a first carrier gas to form a second gaseous stream comprising first carrier gas and the solute. The second gaseous stream derived from the first trap is passed to a second adsorbent-containing trap and solute is trapped therein. Thereafter the second trap is simultaneously heated and backflushed with a second carrier gas to form a third gaseous stream comprising a carrier gas and solute wherein the ratio of solute to carrier gas is greater than the ratio of solute to carrier gas in the second gaseous stream.

19 Claims, 2 Drawing Figures

ISOLATION AND CONCENTRATION OF SAMPLE PRIOR TO ANALYSIS THEREOF

BACKGROUND OF THE INVENTION

1. Field of the Invention

This invention relates to a method and device for the preparation of a solute (herein defined as a material which may comprise one or more components) that it is desired to isolate and purify for induction into analytical instruments such as cas chromatographs (GC), ultra-violet (UV) and infra-red (IR) spectographs, etc. In accordance with this invention a solute, liquid or gas is prepared to a sufficient level of concentration and purity for facile analysis, even when such solution exists in a solvent/matrix in the low parts-per-billion (ppb) range; that is, the picogram range. The concentrating/purifying process of this invention is accomplished by use of a serial, sequential, differential trapping arrangement which allows the solvent, which may be liquid or gas, to pass through to vent while retaining the solute. The solute is then backflushed/heat-desorbed from the trapping system and transferred to another analytical device, generally a gas chromatograph (GC), where it may be analyzed. When a GC is used, either packed or capillary columns may be used as a component separating device.

2. Description of the Prior Art

At present, the state-of-the-art relating to trace analysis in the low ppb range, utilizing traditional gas chromatography techniques with existing hardware and materials, generally has been inadequate, sometimes requiring extensive and time consuming methods which are costly. In many cases low ppb range analyses is not capable of economic attainment by available standard methods.

The major constraint to low-ppb analysis, following conventional gas chromatographic practice, is column capacity. Typically, the maximum sample size that normally can be inputted to a gas chromatograph column is 10 $\mu$l liquid or 5 cc gas. When the solute: solvent ratios are extremely low, the foregoing sample sizes may not contain enough of the solutes(s) for measurement. This of course is dependent on sample size versus detector sensitivity. Larger sample sizes frequently result in solvent interference, peak spreading, poor resolution, etc., thereby precluding satisfactory analysis.

The prior art has not heretofore appreciated that utilization of a series of serial sequentially connected traps operated in the differential trapping mode, provides increased solute purity and the ability to increase solute sample size. When coupled with appropriate monitoring and control means, the differential trapping system can provide a high order of analytical data for solute(s) contained within the broad spectrum of physically divergent samples.

The use of multiport valve-trap arrangements has heretofore been employed (see e.g. U.S. Pat. Nos. 3,955,924; 3,847,546) and multiple arrangements of such multiport valve-trap systems have been used both in parallel (see U.S. Pat. No. 3,693,403) and in series (See U.S. Pat. No. 3,545,255); however, the art has not heretofore appreciated that concentration of solute(s) within a sample could be effected in a highly facile and advantageous manner by utilizing serial, sequential differential trapping to obtain a high order of concentrate along with good sample purity and integrity to perform an unimpeded analysis.

SUMMARY OF THE INVENTION

In its broadest aspect this invention relates to a method and device for the preparation of a solute (herein defined as a material which may comprise one or more components), that it is desired to isolate and purify for induction into analytical instruments such as gas chromatographs (GC), ultra-violet (UV) and infra-red (IR) spectographs, etc.

When used herein, solute and solvent denote components of a sample. The solute which may comprise one or more compounds is the component of the sample which it is desired to isolate. The term solvent and matrix are used interchangeably to distinguish between fluid (liquid or gas) and solid.

Traps which are suitable for use in this invention are packed adsorbent tube traps which have the ability to adsorb and desorb their contents quantitatively.

The desorption of solute from the traps is accomplished by simultaneous heating and backflushing with a carrier gas, this procedure being referred to herein as backflushing/heating.

The carrier gas is generally a gaseous material which will pass through the entire system without undergoing change in composition and/or adversely affecting flame detector operation. Well-known examples of carrier gases meeting the foregoing requirements are helium, argon and nitrogen.

The term narrow-band slug is a term of art which is used to represent a gaseous stream that has a high ratio of solute to carrier gas. The narrower the band of the slug; that is, the higher the ratio of the volume of solute to volume of carrier gas, the greater the efficiency of the analytical instrument, e.g., a chromatograph column/detector.

It is an object of the present invention to provide a method and device for isolating and purifying solute present in samples inclusive of picogram levels, whereby measurement thereof may be effected in presently existing equipment such as vapor phase chromatographs and especially chromotographs utilizing capillary columns.

Another object is to provide diagnostic capability during the concentrating method including the capability of monitoring both solvent elution and solute breakthrough during entrapment, thereby providing the capability of avoiding solute loss.

A further object of this invention is to provide a facile means for saving a portion of the solute being examined on an auxiliary adsorbent tube. In this manner the solute may be recovered by desorption and repetitively reintroduced into the system for purification and retesting.

Yet another object of this invention is the development of a method and system providing for sample isolation, purification and analyses in a facile and economical manner.

Further in this regard, yet another aspect of the instant invention pertains to the manner of determining the optimal time sequence for effecting the adsorption-desorption cycle in trapping and recovering of solute present in a gaseous stream which is made up of carrier gas and a carried sample comprising the solute. The trap utilized is an adsorbent packed tube which preferentially adsorbs the solute. One aspect of the determination is accomplished by diverting to the flame ionization detector (FID) on a continuous basis, a small aliquot portion (suitably about 1% to about 5%) of the gaseous stream simultaneously as it is passed into the first trap. The aliquot portion is passed to the flame ionization detector, whereby it is possible to ascertain the period of time required for the sample to be carried onto the trap. The operator obtains this information by referring visually, suitably to a strip chart recorder associated with the FID. Upon identification of the time required under given conditions of introduction of sample into the trap a minimum time for trapping is established. The other aspect of the determination is accomplished diverting a portion (suitably about 1% to about 5%) of the eluting solvent or solute flowing from the trap to the FID in order to ascertain break-through/elution of solvent and solute.

The information so obtained is useful for a multitude of purposes. First, if the time required for trace component breakthrough is less than the time required for passage of the entire sample into the trap, one is appraised of the fact that under the given conditions the trap selected is unsatisfactory. Second, the FID system allows the operator visually to determine when solvent elution has reached the level where adsorption can be terminated.

Since an important aspect of this invention is specifically directed toward sequential trapping for the purpose of concentrating a solute as a precurser to chromatographic analysis, duplication of results are essential because as will be at once appreciated, interpretation of results of analyzer equipment is made by calibration and comparison with standard samples and the correlation of measurements of the sample being tested with the standard sample is dependent upon the ability to duplicate the respective analysis procedures. The occurrence of break-through of solute, therefore, is to be avoided.

One embodiment of the invention relates to a a method for increasing the ratio of solute to carrier gas in a gaseous stream containing a carrier gas and a sample comprising solute. A first gaseous stream comprising said sample is formed and at least an aliquot portion of the first gaseous stream is passed into a first adsorbent-containing trap, trapping the solute herein. Thereafter the first trap is simultaneously heated and backflushed with carrier gas to form a second gaseous stream comprising first carrier gas and the solute. The second gaseous stream from the first trap is passed directly (without intervening analysis or treatment) to a second adsorbent-containing trap and the solute is trapped therein. Thereafter the second trap is simultaneously heated and backflushed with carrier gas to form a third gaseous stream comprising carrier gas and solute wherein the ratio of solute to carrier gas is greater than the ratio of solute to carrier gas in the second gaseous stream. The first carrier gas and the second carrier gas are generally of the same composition and preferably are passed through the system from a common source.

The third gaseous stream is suitably passed to a vapor phase chromatograph for chromatographic analysis thereby. Retention time within a trap during trapping of the solute was observed to decrease with increasing sample size. Accordingly, by use of a plurality of traps (two or more e.g., 3, 4 etc.), it is possible to substantially concentrate a solute within a sample. Using a plurality of sequential traps to provide sample concentration permits the use of a capillary trap as the final trap and, therefore, the instant method is specifically adaptable for use in combination with a capillary vapor phase chromatograph. The first trapping means is preferably a non-capillary adsorbent-packed tube, the second trap is a capillary or small bore adsorbent-packed tube, the vapor phase chromatograph is a capillary tube chromatograph and the third gaseous stream is passed from the second trap to the chromatograph through a capillary or small bore transfer tube.

The first gaseous stream may be comprised of sample and a third carrier gas and the first gaseous stream may be divided into two aliquot portions, the first aliquot portion suitably being passed into the first adsorbent-containing trap to form the second gaseous stream; and, the second aliquot portion being saved by passing the same into a sample saving tube containing adsorbent which has the ability to retain at least the solute portion of the sample and generally the entire sample. The saved sample is desorbed by passing a carrier gas through the sample saving tube to form a gaseous stream of carrier gas and the saved sample. This gaseous stream is thereafter treated in like manner as the first gaseous stream.

The first gaseous stream may be passed into said first trap by drawing the first gaseous stream therein utilizing a vacuum.

Where the sample comprises solute and solvent and the adsorbent utilized adsorbs the solute preferentially to the solvent, an aliquot portion of the second gaseous stream eluted during trapping may be passed to a flame ionization detector to determine if solute breakthrough occurs. Adsorption should be discontinued prior to solute breakthrough. The flame ionization detector also serves to indicate when solvent elution has been completed. In this manner it is possible to establish a predetermined time whereupon adsorption is terminated and simultaneous heating and backflushing of the first trap is initiated. An aliquot portion of the second gaseous stream may also be diverted before passage into the second trap and passed to a flame ionization detector to determine completion of desorption of solute from the first trap. In this manner the desorption time may be predetermined.

BRIEF DESCRIPTION OF THE DRAWINGS

The novel features that are considered characteristic of this invention are set forth with particularity in the appended claims. The invention, itself, however, both as to its apparatus and method, as well as additional objects and advantages thereof, will best be understood from the followind description when read in connection with the accompanying drawings in which FIG. 1 is the flow diagram of the device for concentrating solute(s) within a sample matrix (solvent) where the solute(s) is present in low nano or picogram levels and in which

DESCRIPTION OF THE PREFERRED EMBODIMENTS

Figure 1:
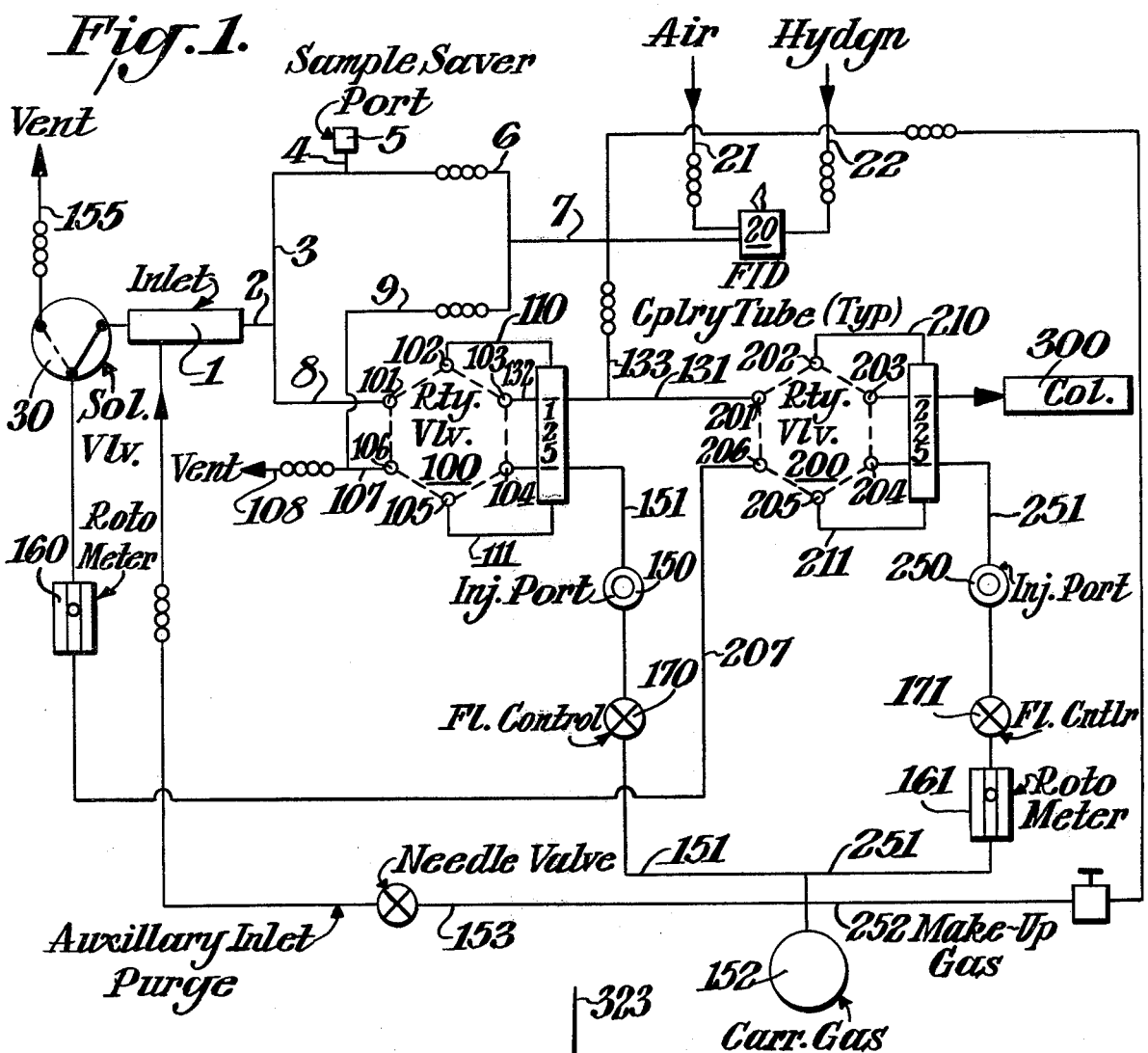

The system of this invention is capable of purifying a solute such that the solvent or matrix with which the solute is associated shall not interfere in the analysis of said solute. This concentrating device is capable of increasing the level of solute concentration while maintaining high purity, and is able to separate the solute from the matrix (solvent) in which it is dissolved, contained or adsorbed on. These solvent materials may be in gaseous, liquid or solid form.

Included in the device of this invention is an inlet means which can accept samples which are:

(1) gaseous, i.e., an ambient atmospheric air sample or the headspace gas above a liquid or solid;

(2) liquid, i.e., a $H_2O$ sample which contains contaminents which could be purged out by a gas and other types of solvent samples which contain components of interest, such as benzene in carbon disulfide; and (3) adsorbed on a sorbent tube which has been used to collect gaseous products, i.e., vinyl chloride on charcoal sorbent tube.

The inlet means is adapted to accommodate the particular form of the sample. It allows for sample introduction by means of:

(1) a syringe, gas sampling valve, vacuum, etc., for any sample which exists in a gaseous state;

(2) a purging-type device whereby the components of interest are purged out of a contained matrix, such as an aqueous solution, and into the inlet by a gas, e.g., air, $N_2$, He, etc.; and, (3) a sorbent-type tube on which the components of interest have been adsorbed. These components are generally desorbed in the inlet by allowing a gas to flow over the sorbent material, frequently applying heat to reduce the time necessary to perform this function.

The system includes a first trapping means to separate solute from at least a portion of the solvent, retain the solute, and vent the non-trapped portion of the solvent. This first trapping means has the capacity to accept very large samples, which may be collected over extended periods of time, avoiding solute breakthrough. The first trapping means suitably contains adsorbent packing materials, generally porous polymers like "TENAX-GC", "PORAPAKS", etc., but may also comprise adsorbents which will obtain the required effect of retaining the components of interest on the first trapping means and expelling out to vent those unwanted constituents, i.e., solvents. Such adsorbents as glass beads, silica gel, charcoal, Se 30, OV 101, etc., are routinely used in GC practice, and are acceptable adsorbent trapping materials for use in the device of this invention.

The system also includes a second trapping means, containing adsorbent packing materials such as hereabove described which may serve to further reduce solvent content. In accordance with this invention, at the second trapping stage an internal standard may be introduced for later use during the GC analysis.

The second trapping means may be capillary or small bore tubing to facilitate high velocity backflushing of the solute at the low flows (2–4 $\mu l$/min.) required when using capillary GC columns. By small bore, it is meant to include tubes of from about 0.04 to about 0.12 inches i.d. Capillary tubes generally have an interior i.d. of from about 0.01 to about 0.04 inches. The ability to use a small bore trapping means is enabled by the use of a multiple sequential trap arrangement wherein a first non-capillary trapping means purifies the solute by removing the major portion of the solvent prior to introduction of solute into the small bore trapping means. Concentration of large amounts of raw sample may or may not be necessary for capillary column analyses; however, removal of solvent is most desirable for maximum efficiency of capillary columns. Because of the function of the first and second trapping means, capillary columns no longer require the use of splitter-type injection systems, as is currently a state-of-the-art requirement.

The first and second trapping means can be held at ambient or raised ambient temperature in order to facilitate the required differential trapping.

After each trapping cycle of the first and second trapping means the flow is reversed to effect backflushing while simultaneously the traps are rapidly heated suitably within about 12 to about 15 seconds, to a temperature ranging from about 200° to about 250° C. above the base trapping temperature. The rapid heating and backflushing causes the collected solute to form a narrow-band, desorbed slug which will then be transferred to the next trapping means or to the analytical instrument desired, suitably a GC column.

For example, during sparging of a water sample, carrier gas percolates through the water and becomes satured with both water vapor and the desired solute. The water in the carrier gas now becomes a continuous contaminant of the carrier gas flow and the first trap is unable to eliminate all the water because it continuously flows into and through the trap. After the solute has been purged from the water, the trap is backflushed/heated utilizing carrier gas which has not been passed through the water sample and, therefore, is water free. The solute is eluted from the first trap in the form of a narrow-band slug which contains water residue from the trap and plumbing. Upon introduction of the narrow-band slug into the second trap, the second trap will respond by trapping the solute and eluting the residual water vapor. Thereafter when the trap is backflushed/heated a second solute slug of substantially narrower-band than previously eluted from the first trap is obtained. Additionally, the solute from the second trap is now virtually water free. In this manner it is possible to introduce the solute, a solute derived from an aqueous type sample, into water-sensitive analyzing devices such as certain chromatographic columns and electron capture detectors.

As will at once be apparent because the first and second trapping means, together produce an extremely narrow-banded slug of solute which is practically solvent free, chromatographic analysis is effected at optinum efficiency with virtually no solvent interference. The column means may be either integral or external to the system. The device of this invention, the concentrator, may be an ancillary device for an external gas chromatograph which contains its own separating column and detector, in which case it will be coupled to the GC. For this purpose a small bore tube transfer line is advantageously employed. Alternatively, the concentrator can also contain its own integral column means utilizing either its own integral analytical detector and/or an external detector.

A detector means is included to provide diagnostic information used to set up operating parameters. While the detector means may be used quantitatively and/or qualitatively, its essential functions are to provide the following:

(1) an initial response at introduction of most sample types;

(2) an indication of when the solvent has passed through the first trapping means and out to vent, thereby allowing determination of the initial time required to sparge or purge the sample;

(3) an indication of solute breakthrough from the trapping system, should it occur;

(4) a semi-quantitative measurement of collected solute passing through the system used to correctly set attenuation controls;

(5) a description of the efficiency of the trapping system during backflushing/heat-desorption cycles; and a (6) warning of mechanical or chemical malfunctions should they occur at any point in the concentration cycle.

A first carrier gas means transports the sample from the inlet means through the first trapping means, to the detector means, and into the second trapping means. A second carrier gas carries the sample into the second trapping means during its backflush/heat-desorption cycle, onto the column means, and back to the detector means.

The flame ionization detector, as in other systems is associated with an electrometer means for amplifying the electrical signal emitted from the detector means and transferring said signal to an external device for visually recording a chromatogram.

For purpose of explaining this invention and referring to FIG. 1 a sample to be analyzed is introduced through inlet 1 in the form of a gas sample. The sample is an air mixture containing approximately 1% acetone and 1 ppm benzene. This sample is introduced by way of a gas syringe containing 100 cc volume. The sample is injected through inlet 1 by means of an injection port, whereupon the sample exits to line 2 and splits to lines 3 and 8. Because the sample size is quite large relative to the plumbing dead volume, the sample is displaced throughout the entire system without need of the carrier gas at this point.

The sample splits such that 91.3 cc is carried through line 3 while 8.7 cc passes through line 8. Line 3 is then split such that line 4, which is associated with the sample saver receptical and a sorbent tube, recovers 87 cc of the original 91.3 cc, allowing further analyses from the same sample. The remaining 4.3 cc of the original 91.3 cc continues to the Flame Ionization Detector (FID) 20 which is fed air and hydrogen via lines 21 and 22 in conventional manner and which indicates that an injection has been made (see FIG. 2, No. 320). The FID senses the presence of the organics contained in the air sample (benzene and acetone) due to the fact that the hydrogen flame ionizes these organics by burning. This ionization provides an electrical output which is suitably plotted as is common in the art on a strip chart recorder to provide a visual indication that an injection has been made.

The 8.7 cc of sample which passes through line 8 continues through valve 100 and onto its trap 125 associated therewith because the valve is in the "trap in" position (which will be explained in more detail hereinafter) which position is used for gas injection samples. Here most of the air, due to the low internal volume of the tubing used for passage of gas between the components of the system and the trap's inability to stop air, will immediately pass to vent. It is to be noted that FID 20 responds only to organic materials and therefore the recorder does not respond to elution of air. The benzene and the acetone, which is unwanted, remain on the trap due to the trap's ability to hold onto these components for this volume of sample, lacking initiation of carrier gas flow which operates to transport these compounds further down the adsorbent within the trap. Therefore, trap 125 contains all of the benzene and acetone and a fraction of the original air.

After the 100 cc injection has been made the solenoid valve, which during injection was held in the vent position, is now actuated to allow the carrier gas flow originating from flow controller 170 to pass through inlet means 1 and then pass through the same lines as previously described. Each line will have the same proportion of carrier flow as described earlier for the injected sample. The flow of carrier gas through line 8 immediately purges the remaining air from the trap and in time will (due to using a select trapping material such as TENAX) cause the acetone, which is an unwanted solvent in this case, to pass from the trap while at the same time the benzene which has very little tendency to migrate through the packing material is retained in the trap. The acetone, as it passes from the trap to line 107, splits such that 10% of the acetone which exits via line 107 is diverted via path 9 and to FID 20 where the signal generated from the ionization of acetone is visually recorded (see FIG. 2, No. 321). The remaining 90% of the acetone eluted from the trap passes to vent via line 108. Note, that since the FID is very sensitive to small amounts of organic material, only a small fraction is required (10%) to indicate this elution.

Figure 2:
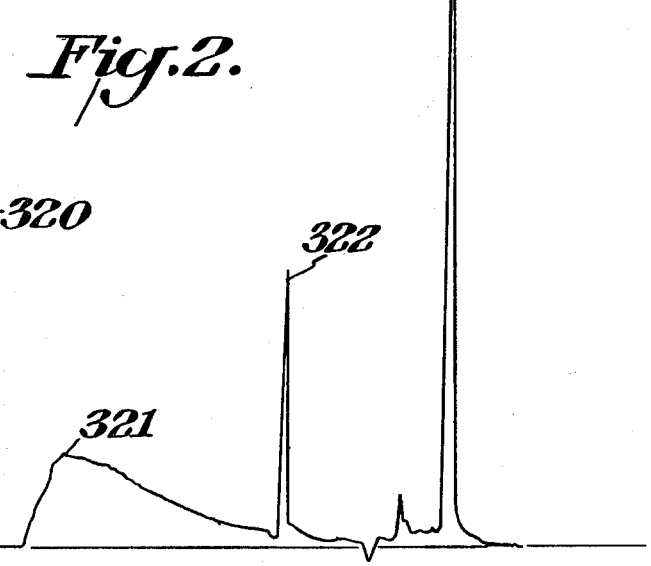
FIG. 2 is a typical chromatogram.

The initial carrier gas inlet flow time required to purge the solute from the trap corresponds to the time required for the FID to no longer detect the presence of material eluting from the trap. When all or most of the acetone is removed, valve 100 is advanced (this like other valve rotations may be accomplished automatically) and rotates so that alternate ports are internally connected. This repositioning of the ports initiates the backflushing sequence and causes carrier flow to enter the trap in a direction opposite the flow of acetone and benzene during adsorption. This reversing of flow and the carrying of the sample off the trap in the opposite direction of adsorption is herein referred to as backflushing. Simultaneously with rotation, the trap 125 is heated (within 12-15 seconds) to a temperature about 225° C.-250° C. above its base temperature. This heating rate causes the solute (benzene) to be purged off in a narrow-band slug. This slug is passed from trap 125 to valve 200 which is in the "trap in" configuration. About 10% of the benzene (solute) slug splits to line 133 which is connected to the FID, allowing a response to be recorded again (see FIG. 2, No. 322). This response may be referred to as the total organic carbon response (TOC) which represents the total organic material passing from one trap to another. Although not directly quantitative or qualitative, the TOC provides an indication of the relative response which might be expected in a subsequent GC analysis and also provides a visual indication of trap efficiency, which is denoted by a gaussian type peak with little or no tailing as illustrated in FIG. 2, No. 322.

This trap transfer also allows for an internal standard to be introduced through injection port 150 (onto trap 225 along with the collected solute) in case qualitative or quantitative data is required during GC analysis.

After a predetermined period which depends on sample type and in this instance is preferably between about 2 and about 5 minutes, trap 225 is backflushed by rotating valve 200, thereby reversing the flow of carrier gas into trap 225 while simultaneously heating the trap to 225° C.-250° C. above the initial temperature of adsorption, said heating being effected within 12-15 seconds. The solute is desorbed in the form of a narrow-band slug which is more narrow than the slug derived from trap 125. This slug is transferred to a GC column for analysis. The slug is free of air and acetone solvents, leaving only the pure benzene for an unobstructed and enhanced concentration level. The analysis will now benefit from the removal of the foregoing solvents which interfere with chromatograph analysis and by the concentration of the benzene contained in the original 100 cc sample. (See FIG. 2, No. 323)

A sample saver tube hereinafter referred to as sample saver tube A which is associated with sample saver 5 contains 87% of the 100 cc sample injection previously described. Saver tube A may now be taken from its receptical, sample saver 5, and placed inside inlet means 1 for further analysis. A second sorbent tube hereinafter referred to as sorbent tube B is then placed in the sample saver receptacle 5. The first-mentioned sorbent tube A may thus be heat-desorbed of its contents and the heat-desorbed effluent which no longer has air associated therewith may then be treated in the manner previously described for the original sample. 87% of the content from sorbent tube A is now collected on sorbent tube B for further analyses. Sorbent tube B can now be interchanged with sorbent tube A and placed in inlet means 1. It will be noted that sorbent tube A is now free of any solute or solvent because of previous desorption while in inlet means 1. Sorbent tube A, therefore, can be replaced in the sample saver receptical to function as a sample saving tube during the next desorption, which desorption will be from sorbent tube B.

Where the foregoing procedure is adopted less sample remains after each succeeding run; therefore, the test results are correlated by adjusting the results in conformance with the following equation:

$$T_{int} = \frac{\text{ppm found}}{(\% \text{ saved})^{N-1}(\% \text{ analyzed})}$$

$T_{int}$ = (ppm) in the original sample
ppm = calculated ppm from GC analysis
% saved = % saved by sorbent tube (87%)
% analyzed = % analyses (8.7%)
N = run number The two sorbent tubes, sorbent tubes A and B are matched in restriction, but not necessarily composed of the same adsorbent material. This method restriction maintains the same ratio of flow within the system and thereby allows for correlation of sequential runs in accordance with the formula set forth and discussed above.

The flow diagram can best be described by a description of the flow of the carrier gas as it leaves 3-way solenoid valve 30 and enters inlet means 1. Valve 100 will initially be in a "trap in" or "trap out" position prior to any introduction of sample, dependent on the type of sample to be introduced. In the "trap in" position, carrier gas and sample flow through inlet 1 to line 2 whereupon the flow splits into two paths, lines 3 and 8. For purposes of further detailed illustration of the process, operation utilizing sample saver 5 is used. The initial split via line 2 depends on the total downstream restriction of lines 3 and 8, which under normal conditions will be 91.7% for line 3 and 8.7% for line 8. Following passage through line 3, the carrier gas (and sample) undergoes a secondary split through lines 4 and 6, and here again the split depends on each line's downstream restriction. In the case illustrated line 4 is coupled to sample saver 5 with a sorbent tube installed in sample saver 5. The sorbent tube receives 87% of the total flow via line 2 and line 6 receives 4.3%. Line 6 connects with line 7 which is in turn connected to FID 20. Line 8 receives 8.7% of the total carrier flow/sample. Thus 87%+4.3%+8.7%=100% of the total flow/sample originating from line 2.

In the "trap-in" mode line 8 is connected to port 101 of valve 100. Port 101 is internally connected to port 102 which is connected to line 110 and trap 125. The flow/sample exits via line 111 to port 105 which is internally connected to port 106 which in turn connects with line 107 which in turn splits to lines 108 and 9. The carrier gas/sample split ratio again depends on the downstream restriction. Generally this split may be approximately 9:1 with the largest flow going to vent. Line 9 is connected to line 7 which is connected to FID 20.

The carrier flow originates at gas source 152 which flows through four lines, 153, 151, 251 and 252. Line 153 is an auxiliary inlet flow which is used to keep the inlet purged of contaminants. Line 252 is an auxiliary flow to make up a required flow loss for the FID when a GC column is not an integral part of the system and for low flow columns such as capillary columns. Line 51 includes a flow controller 170 to maintain constant total carrier gas flow regardless of varying downstream restriction changes. Line 151 also includes an injection port 150 which allows for internal standards to be injected onto trap 225 with the collected sample. Line 251 carries the carrier gas used for desorbing (backflushing) trap 225 and supplies the flow for the GC column 300 or the transfer of the sample to an external GC column or other type equipment. It also contains a flow controller 171 and injection port 250, all of which can be flow monitored by rotometer 161. Port 250 allows the chromatographic column to be operated in the normal manner, bypassing the trapping system.

In accordance with the flow arrangement associated with the six-port valves under either "trap in" or "trap out" conditions three alternate internal flow paths exist in each position. With particular reference to valve 100 in the "trap in" position ports 101 and 102 are internally connected, ports 103 and 104 are internally connected and ports 105 and 106 are internally connected. In all modes of operation other than the backflushing/heat-desorption of solute from trap 225, valve 200 will always be in the standby or "trap in" position described herebelow. During the initial processing of the sample through valve 100 to valve 200 ports 201 and 202 are internally connected, ports 203 and 204 are internally connected, and ports 205 and 206 are internally connected. During backflushing/heat-desorption of trap 125 the "trap out mode", ports 101 and 106 are internally connected, ports 104 and 105 are internally connected, and ports 102 and 103 are internally connected. Rotary valve 200 exhibits the same internal port changing as valve 100 when operated in the backflushing-/heat-desorption mode.

In the "trap in" mode, carrier gas passing through line 151 enters valve 100 at port 104 which is internally connected to port 103 which is connected to line 132 which then splits to lines 133 and 131. The flow to each respective line is again dependent on each line's total downstream restriction. The carrier gas/solute leaving through line 132, allows about 8% of the total flow to pass to line 133 and 92% to pass to line 131, valve 225 being in the normal "trap in" position. Line 133 is connected to FID 20. Line 131 is connected to port 201 of valve 225 which in the "trap in" position is internally connected to port 202 which is connected to trap 225 via line 210. Line 211 connects trap 225 to port 205 which is internally connected to port 206. Line 207 connects port 206 and solenoid valve 30. This path contains rotometer 160. Line 155 is the standby vent path for flow originating from line 207 when the sample inlet is not in use.

This system contains valves 30, 100, and 200. Valve 30 is suitably an electrically operated 3-way valve which is primarily used to introduce flow through the inlet during the sample introduction stage and which returns to a vent position upon conclusion of sample introduction, thus stopping flow through inlet means 1. Valve 100, along with its associated trap 125, is used to perform the primary differential trapping. It is this valve/trap combination which must perform the first step of solute collection and purification. Upon conclusion of sample introduction, valve 100 transfers the contents of trap 125 via valve 200 to trap 225. This transfer is effected by backflushing and rapid heat-desorption, whereupon trap 125 deposits its previously collected contents via valve 200 to trap 225, which may operate to further purify the solute. Trap 225 normally obtains the sample in a much more refined form than trap 125, due to the fact that trap 125 may require rather lengthy sample collection time, i.e., a purge of water samples may last for 15 minutes. On the other hand trap 225 will only require short periods of time (2-5 min.) depending on sample type; therefore, the adsorbent trap capacity required for trap 225 is lessened, and thus allows for the use of a small bore type trap which may contain 1/20 the amount of sorbent material contained in the first trap. Such a trap is required when capillary columns are used for GC analysis because capillary columns require low flows (2-4cc/min.) to obtain maximum efficiency. Large bore traps therefore are unsatisfactory because they do not allow for rapid removal of trapped components due to the low linear velocity which would occur at 2-4cc/min. in a large bore tube. In the instant invention which allows for entrapment on a small or capillary bore tube trap, low flows establish a high linear velocity through the foregoing traps thus in turn transferring solute at high linear velocity to capillary-type GC columns. Current state of the art trapping, which employs only a single trap, in order to allow adsorption without sample loss over extended periods of time and at the same time provide for operable desorption flow to capillary GC columns, now generally employs precolumn sub-ambient trapping. In accordance with this invention such cold trapping is unnecessary.

Because of the specific valving arrangements provided in the device of this invention, the invention is particularly well adapted for purification and isolation of a sample comprising solute and solvent both of which are adsorbed on the trap. When such a sample is introduced into the system the process is initially operated in the following manner: A precolumn tube which contains suitable separating GC type material, e.g., glass beads is inserted into the sample introduction means. Sample is injected with trap 125 in the "trap out position". Gross separation of solvent from solute occurs. Carrier gas is passed through the precolumn tube and carries the solvent out to vent while solute is retained within the precolumn tube. Once solute is isolated valve 100 is returned to the "trap in" position, whereupon the precolumn is heated and sample is eluted to trap 125 with a carrier gas, processing thereafter being effected in the same manner as other samples. An example of such a sample would be pesticides in water.

The system of this invention is also adapted for head space analysis, ambient air monitoring and other type long term uninterrupted studies of solute content. In these cases generally the solute is present in very low trace levels at the picogram level. The system may be operated under vacuum or positive pressure and is operated without carrier flow during sample introduction. In this mode solenoid valve 30 is not used with vacuum or external pressurized systems but may be used for pressurized "head space" systems. Sample introduction is in the "trap in" mode and upon completion of desired solute collection time, which depends upon the level of concentration and detection systems, processing is thereafter conducted in the same manner as other samples.

The transfer lines, capillary tubing, chromatograph tubes, valves and other parts of the apparatus may be made of glass, metal such as stainless steel, plastic or other material selected to be suitable for the particular samples and carrier gases utilized.

It will be obvious that various modifications may be made in the apparatus and in the manner of operating it. It is intended to cover such modifications and changes as would occur to one skilled in the art, as the following claims permit and consistent with the state of the prior art.

I claim:

1. A method for increasing the ratio of solute to carrier gas in a gaseous stream containing a carrier gas and a sample comprising solute, which method comprises:
   (a) forming a first gaseous stream comprising said sample;
   (b) passing at least an aliquot portion of the first gaseous stream into a first adsorbent-containing trap and therein trapping said solute; and, thereafter
   (c) simultaneously heating and backflushing said first trap with a first carrier gas to form a second gaseous stream comprising first carrier gas and the solute;
   (d) passing said second gaseous stream from said first trap to a second adsorbent-containing trap and therein trapping said solute; and, thereafter
   (e) simultaneously heating and backflushing said second trap with a second carrier gas to form a third gaseous stream comprising a carrier gas and said solute wherein the ratio of solute to carrier gas is greater than the ratio of solute to carrier gas in said second gaseous stream.

2. The method of claim 1 further characterized in that the first carrier gas and the second carrier gas are of the same composition.

3. The method of claim 1 further characterized in that the third gaseous stream is passed to a vapor phase chromatograph for chromatographic analysis thereby.

4. The method of claim 3 further characterized in that the first trapping means is a non-capillary adsorbent-packed tube, the second trap is a capillary or small bore adsorbent-pcked tube, the vapor phase chromatograph is a capillary tube chromatograph and the third gaseous stream is passed from the second trap to the chromatograph through a capillary transfer tube.

5. The method of claim 1 wherein the first gaseous stream is comprised of sample and a third carrier gas.

6. The method of claim 5 further characterized in that the first gaseous stream is divided into two aliquot portions, the first aliquot portion is passed into the first adsorbent-containing trap to form the second gaseous stream; and, the second aliquot portion is saved by passing said second aliquot portion into a sample saving tube containing adsorbent wherein said sample is retained.

7. The method of claim 6 further characterized in that the saved sample is desorbed by passing a carrier gas through the sample saving tube to form a gaseous stream of carrier gas and saved sample.

8. The method of claim 1 further characterized in that the first gaseous stream is passed into said first trap by drawing said gaseous stream therein utilizing a vacuum.

9. The method of claim 1 wherein the sample comprises solute and solvent and the adsorbent adsorbs said solute preferentially to said solvent further characterized in that an aliquot portion of the second gaseous stream eluted during trapping is passed to a flame ionization detector to determine if solute breakthrough occurs and when solvent elution has been completed, whereupon adsorption is terminated and simultaneous heating and backflushing of the first trap initiated.

10. The method of claim 1 further characterized in that an aliquot portion of the second gaseous stream is diverted before passage into the second trap and passed to a flame ionization detector to determine completion of desorption of solute from the first trap, whereupon desorption is terminated.

11. A device for increasing the ratio of solute to carrier gas in a gaseous stream containing a carrier gas and sample comprising solute, which device comprises:
   (a) sample inlet means for providing a first gaseous stream comprising said solute;
   (b) a first adsorbent-containing trap for trapping said solute;
   (c) means for passing at least an aliquot portion of said first gaseous stream from said inlet means to said first trap;
   (d) first backflushing means for passing carrier gas through said first trap simultaneously with the heating thereof to desorb solute contained therein and to form a second gaseous stream comprising said solute and carrier gas;
   (e) a second adsorbent-containing trap for trapping said solute;
   (f) means for passing second gaseous stream from said first trap to said second trap;
   (g) second backflushing means for passing carrier gas through said second trap simultaneously with the heating thereof to desorb solute contained therein to form a third gaseous stream comprising said solute and carrier gas;
   (h) venting means associated with said first adsorbent-containing trap for venting non-adsorbed solvent eluting from said first trap during trapping of solute;
   (i) means for detecting flow of solvent out of vent; and,
   (j) means for passing an aliquot portion of non-adsorbed solvent eluting from said first trap to said detector means.

12. The device of claim 11 further characterized in that the means for detecting said flow of solvent out to vent comprises a flame ionization detector.

13. The device of claim 12 further comprising a means for diverting an aliquot portion of the first gaseous stream prior to passage thereof into the first trap and passing the portion of the first gaseous stream so diverted to the flame ionization detector.

14. The device of claim 12 further comprising a means of diverting an aliquot portion of the second carrier gas prior to passage thereof into the second trap and passing the portion of the second gaseous stream so diverted to the flame ionization detector.

15. A device for increasing the ratio of solute to carrier gas in a gaseous stream containing a carrier gas and sample comprising solute, which device comprises:
   (a) sample inlet means for providing a first gaseous stream comprising said solute:
   (b) a first adsorbent-containing trap for trapping said solute;
   (c) means for passing at least an aliquot portion of said first gaseous stream from said inlet means to said first trap;
   (d) first backflushing means for passing carrier gas through said first trap simultaneously with the heating thereof to desorb solute contained therein and to form a second gaseous stream comprising said solute and carrier gas;
   (e) a second adsorbent-containing trap for trapping said solute;
   (f) means for passing second gaseous stream from said first trap to said second trap;
   (g) second backflushing means for passing carrier gas through said second trap simultaneously with the heating thereof to desorb solute contained therein to form a third gaseous stream comprising said solute and carrier gas; and,
   (h) carrier gas feeding means comprising a single carrier gas source for feeding a carrier gas of the same composition to the first and second traps to effect backflushing of solute from said first and second traps.

16. A device for increasing the ratio of solute to carrier gas in a gaseous stream containing a carrier gas and sample comprising solute, which device comprises:
   (a) sample inlet means for providing a first gaseous stream comprising said solute;
   (b) a first non-capillary adsorbent-containing trap for trapping said solute;
   (c) means for passing at least an aliquot portion of said first gaseous stream from said inlet means to said first trap;
   (c) first backflushing means for passing carrier gas through said first trap simultaneously with the heating thereof to desorb solute contained therein and to form a second gaseous stream comprising said solute and carrier gas;
   (e) a second capillary adsorbent-containing trap for trapping said solute;
   (f) means for passing second gaseous stream from said first trap to said second trap; and,
   (g) second backflushing means for passing carrier gas through said second trap simultaneously with the heating thereof to desorb solute contained therein to form a third gaseous stream comprising said solute and carrier gas.

17. The device of claim 16 further comprising a capillary chromatograph and capillary conduit means connecting said chromatograph and the second capillary trap, whereby backflushed solute is transferred from said second trap to said chromatograph for analysis.

18. A device for increasing the ratio of solute to carrier gas in a gaseous stream containing a carrier gas and sample, which device comprises:
   (a) sample inlet means for providing a first gaseous stream comprising said solute;
   (b) a first adsorbent-containing trap for trapping said solute;
   (c) means for passing at least an aliquot portion of said first gaseous stream from said inlet means to said first trap;

(d) first backflushing means for passing carrier gas through said first trap simultaneously with the heatin thereof to desorb solute contained therein and to form a second gaseous stream comprising said solute and carrier gas;

(e) a second adsorbent-containing trap for trapping said solute;

(f) means for passing second gaseous stream from said first trap to said second trap;

(g) second backflushing means for passing carrier gas through said second trap simultaneously with the heating thereof to desorb solute contained therein to form a third gaseous stream comprising said solute and carrier gas;

(h) sample saving means for saving a portion of the sample contained within the first gaseous stream; and, (i) means for passing an aliquot portion of the first gaseous stream to said sample saving means.

19. The device of claim 18 further characterized in that said inlet means for providing a first gaseous stream is adapted to to accommodate a sorbent tube and said sample saving means comprises a sorbent tube which can adsorb the solute in said sample and is adapted for accomodation within said inlet means, whereby a third gaseous stream derived from said sample tube can be produced in which the ratio of solute to carrier gas is substantially the same as the ratio of solute to carrier gas in the third gaseous stream which is obtained from the first aliquot portion of sample introduced into the device.

* * * * *